United States Patent
Zhang et al.

(10) Patent No.: US 11,932,602 B2
(45) Date of Patent: Mar. 19, 2024

(54) METHOD FOR PREPARING NICOTINAMIDE MONONUCLEOTIDE COCRYSTAL

(71) Applicants: BONTAC BIO-ENGINEERING(SHENZHEN) CO., LTD, Shenzhen (CN); ZHONGSHAN BONTAC BIO-TECHNOLOGY CO., LTD, Zhongshan (CN)

(72) Inventors: Zhang Zhang, Shenzhen (CN); Ming Chen, Shenzhen (CN)

(73) Assignees: BONTAC BIO-ENGINEERING(SHENZHEN) CO., LTD, Shenzhen (CN); ZHONGSHAN BONTAC BIO-TECHNOLOGY CO., LTD, Zhongshan (CN)

( * ) Notice: Subject to any disclaimer, the term of this patent is extended or adjusted under 35 U.S.C. 154(b) by 159 days.

(21) Appl. No.: 17/833,113

(22) Filed: Jun. 6, 2022

(65) Prior Publication Data

US 2022/0411376 A1    Dec. 29, 2022

(30) Foreign Application Priority Data

Jun. 18, 2021    (CN) .......................... 202110677769.7

(51) Int. Cl.
C07D 213/82    (2006.01)

(52) U.S. Cl.
CPC ........ *C07D 213/82* (2013.01); *C07B 2200/13* (2013.01)

(58) Field of Classification Search
CPC .................................................. C07B 2200/13
See application file for complete search history.

(56) References Cited

U.S. PATENT DOCUMENTS

2018/0282362 A1*  10/2018  Carr ..................... C07H 19/048

FOREIGN PATENT DOCUMENTS

| CN | 108697722 A | 10/2018 |
|----|-------------|---------|
| CN | 112538101 A | 3/2021 |
| WO | WO2018047715 | 3/2018 |

* cited by examiner

*Primary Examiner* — Jeffrey S Lundgren
*Assistant Examiner* — Eric Tran
(74) *Attorney, Agent, or Firm* — Muncy, Geissler, Olds & Lowe, P.C.

(57) ABSTRACT

The present disclosure provides a method for preparing a nicotinamide mononucleotide cocrystal, and aims to solve the technical problems of larger content/weight difference and inconsistent quality of nicotinamide mononucleotide (NMN) medicines or health care products due to poor fluidity of existing nicotinamide mononucleotide crystals. The method includes the steps of mixing nicotinamide mononucleotide as an active pharmaceutical ingredient with isonicotine as a cocrystal former by adopting solution synthesis and then performing crystal precipitation. The method has the advantages of simple operation and wide application range.

7 Claims, 2 Drawing Sheets

METHOD FOR PREPARING NICOTINAMIDE MONONUCLEOTIDE COCRYSTAL

TECHNICAL FIELD

The present disclosure relates to the technical field of preparation of compound crystals, in particular to a method for preparing a nicotinamide mononucleotide cocrystal.

BACKGROUND

Nicotinamide mononucleotide (NMN for short) is a biochemical substance inherent in biological cells. It may be adenylated by nicotinamide nucleotide adenosyltransferase in the cells to form an important substance-nicotinamide adenine dinucleotide (NAD for short, also known as coenzyme I, existing in all the cells, taking part in thousands of biocatalytic reactions, and playing an important role in the generation of biological cell energy) that the biological cells depend on for survival. NMN is a direct precursor of NAD. As an important intermediate of an NAD salvage synthesis pathway in biological cells, its level in the biological cells directly affects the concentration of NAD.

Studies have found that supplementing NMN in vitro is a most ideal way to increase the concentration of NAD in cells. In addition, it has also been found that supplementing NMN in vitro may achieve many health care effects of delaying aging, treating Parkinson's and other geriatric diseases, regulating insulin secretion, affecting mRNA expression and the like. Besides, more and more new medical uses of NMN are being reported. In addition, with the news of Li Ka-shing's investment in "elixir" NMN, the NMN has become a favorite for a while and has been favored by many capitals, and the general public is also rushing to pursue NMN medicines or health care products. As a result, the demand for the NMN medicines or health care products is increasing day by day.

Because the stability of NMN is not good enough, medicines or health care products produced from NMN amorphous powder easily lose their pharmaceutical activity during the storage and transportation. Therefore, NMN crystals were developed. For example, two crystal forms of β-nicotinamide mononucleotide were published in Chinese patent application CN108697722A, which are anhydrous crystals (form 1) and dimethyl sulfoxide solvate crystals (form 2) respectively. Nowadays, related enterprises generally adopt NMN in a crystal form to produce NMN medicines or health care products, and the stability of the products has been significantly improved. However, there are still certain problems, such as larger content/weight difference and inconsistent quality of products with poorer fluidity of NMN.

SUMMARY

In view of the deficiencies mentioned in the above background, an objective of the present disclosure is to develop a method for preparing nicotinamide mononucleotide, capable of obtaining nicotinamide mononucleotide crystals with better fluidity, in order to solve the technical problems of larger content/weight difference and inconsistent quality of NMN medicines or health care products due to poor fluidity of existing nicotinamide mononucleotide crystals.

To achieve the objective, the present disclosure provides a method for preparing a nicotinamide mononucleotide cocrystal, including the following steps: mixing nicotinamide mononucleotide as an active pharmaceutical ingredient with isonicotine as a cocrystal former by adopting solution synthesis and then performing crystal precipitation.

The so-called cocrystal, according to the definition in the "Guidelines (2011) for the Regulatory Classification of Pharmaceutical Cocrystals" published by the Food and Drug Administration (FDA), refers to a crystalline substance containing two or more different molecules in a same crystal lattice. Cocrystal components interact through non-ionization and are presented in a neutral state. There are two types of cocrystal components, one is an active pharmaceutical ingredient (API for short), and the other is a cocrystal former (CCF for short). Under the action of hydrogen bonds, π-π stacking, Van der Waals forces or other non-covalent bonds, the two types of cocrystal components are combined in a fixed stoichiometric ratio to generate a new solid form.

Common methods for preparing cocrystals, according to the form of each component during the preparation, are divided into two categories: solution synthesis and solid synthesis. The so-called solution synthesis refers to that both the API and the CCF are in a fluid state during the synthesis, including evaporative crystallization, cooling crystallization, suspension and the like. The so-called solid synthesis refers to that both the API and the CCF are in a solid form during the synthesis, including sublimation, melting and grinding.

When the cocrystals are prepared by adopting the solution synthesis, the stoichiometric ratio of the API to the CCF will affect the amount of cocrystal precipitation. If the stoichiometric ratio is not appropriate, one of the substances may be precipitated alone, thereby affecting the cocrystal precipitation rate. In the above method for preparing a nicotinamide mononucleotide cocrystal provided by the present disclosure, the nicotinamide mononucleotide and the isonicotine are preferably mixed in a molar ratio of 1:1, so that the nicotinamide mononucleotide-isonicotine cocrystal may be precipitated to the greatest extent.

In the above method for preparing a nicotinamide mononucleotide cocrystal provided by the present disclosure, the processes of mixing and crystal precipitation are both performed in a mixed system of an organic solvent and water. The type of the organic solvent in this method plays a key role in whether the crystals may be smoothly precipitated. In the above method for preparing a nicotinamide mononucleotide cocrystal provided by the present disclosure, the organic solvent is preferably tetrahydrofuran, acetonitrile or acetone.

More preferably, in the above method for preparing a nicotinamide mononucleotide cocrystal provided by the present disclosure, in the mixed system of the organic solvent and the water, a volume ratio of the organic solvent to the water is 1:(1-5).

Preferably, in the above method for preparing a nicotinamide mononucleotide cocrystal provided by the present disclosure, during the mixing, the temperature of the mixed system of the organic solvent and the water is kept at 30-55° C., which not only prepares for the subsequent cooling crystal precipitation, but speeds up the mixing process to save time.

In the above method for preparing a nicotinamide mononucleotide cocrystal provided by the present disclosure, the mixed system of the organic solvent and the water may be obtained by directly mixing the organic solvent with the water or by dropwise adding the organic solvent into the water. For the former way, the nicotinamide mononucleotide and the isonicotine may be added after the organic solvent is mixed with the water; and for the latter way, before the organic solvent is dropwise added into the water, the nicotinamide mononucleotide and the isonicotine should be dissolved in the water.

Preferably, in the above method for preparing a nicotinamide mononucleotide cocrystal provided by the present disclosure, the mixed system of the organic solvent and the water is prepared in the latter way, namely, the nicotinamide mononucleotide and the isonicotine are dissolved in the water before the organic solvent is slowly dropwise added into the water. This method is capable of further increasing the bulk density of crystals, thereby obtaining crystals with better fluidity.

More preferably, in the above method for preparing a nicotinamide mononucleotide cocrystal provided by the present disclosure, during the process of slowly dropwise adding the organic solvent into the water, the temperature of the mixed system of the organic solvent and the water is kept at 30-55° C., which not only prepares for the subsequent cooling crystal precipitation, but speeds up the mixing process to save time.

Preferably, in the above method for preparing a nicotinamide mononucleotide cocrystal provided by the present disclosure, the crystal precipitation process is performed in a state where standing is performed after the temperature of the mixed system of the organic solvent and the water is lowered to 4-8° C.

The inventor has finally developed the above method for preparing a nicotinamide mononucleotide cocrystal provided by the present disclosure through a large amount of long-term experimental exploration and creative work. It has been proved through repeated experiments that the method is capable of successfully preparing a new crystal form of nicotinamide mononucleotide presented in a cocrystal form with a success rate of 100%.

For the nicotinamide mononucleotide-isonicotine cocrystal prepared with the above method for preparing a nicotinamide mononucleotide cocrystal provided by the present disclosure, Cu-Kα radiation is used, and X-ray powder diffraction represented by an angle 2θ has diffraction peaks at about 9.6±0.2°, about 13.3±0.3°, about 22.8±0.2° and about 36.5±0.2°. Moreover, its differential scanning calorimetry analysis diagram has endothermic peaks at 55.8±3° C. and 151.9±3° C.

Further, for the nicotinamide mononucleotide-isonicotine cocrystal prepared with the above method for preparing a nicotinamide mononucleotide cocrystal provided by the present disclosure, Cu-Kα radiation is used, and X-ray powder diffraction represented by an angle 2θ has diffraction peaks at about 9.6±0.2°, about 9.8±0.2°, about 10.6±0.2°, about 13.3±0.3°, about 16.3±0.2°, about 21.3±0.2°, about 22.8±0.2°, about 32.1±0.2° and about 36.5±0.2°.

Experiments find that the nicotinamide mononucleotide-isonicotine cocrystal prepared with the above method for preparing a nicotinamide mononucleotide cocrystal provided by the present disclosure not only does not affect the pharmaceutical activity of nicotinamide mononucleotide, but has a higher bulk density than existing crystals, thereby significantly improving the fluidity of the nicotinamide mononucleotide. The bulk density is related to the characteristics such as the form and particle size of the crystals, and the characteristics such as the form and particle size of the crystals are determined by control conditions such as the steps, the types of solvents, the temperature and the like in the preparation process. Therefore, the obtaining of the crystals with the higher bulk density completely depends on the selection and setting of specific process conditions in the above method for preparing a nicotinamide mononucleotide cocrystal provided by the present disclosure.

The Beneficial Effects

Compared with the prior art, the present disclosure has the following advantages:
1. The present disclosure provides a method for preparing a nicotinamide mononucleotide cocrystal, capable of successfully preparing new crystals of nicotinamide mononucleotide presented in a cocrystal form, which fills the gap of the nicotinamide mononucleotide cocrystal, and the method is simple to operate and wide in application range.
2. Experiments find that the nicotinamide mononucleotide-isonicotine cocrystal prepared with the above method for preparing a nicotinamide mononucleotide cocrystal provided by the present disclosure not only does not affect the pharmaceutical activity of nicotinamide mononucleotide, but has a higher bulk density than existing crystals, thereby significantly improving the fluidity of the nicotinamide mononucleotide. Therefore, the technical problems of larger content/weight difference and inconsistent quality of NMN medicines or health care products in the production of enterprises may be well solved.
3. The present disclosure provides a preparation method capable of increasing the bulk density of nicotinamide mononucleotide crystals.

DETAILED DESCRIPTION OF THE EMBODIMENTS

Figure 1:
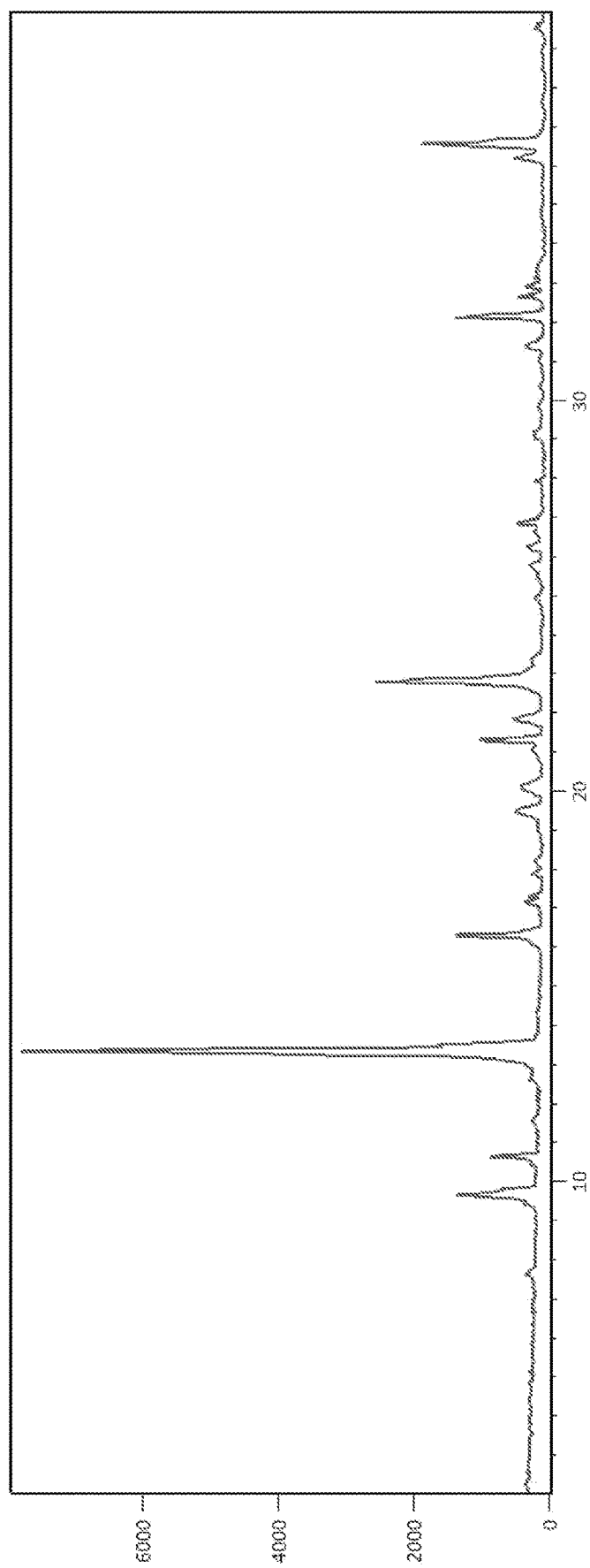
FIG. 1 is an X-ray powder diffraction spectrum of a nicotinamide mononucleotide-isonicotine cocrystal provided by the present disclosure.

The present disclosure is further described in detail below with reference to the accompanying drawings and specific examples. The following examples are to explain the present disclosure. The present disclosure is not limited to the following examples.

Raw materials and reagents used in the following examples were all purchased from the market, unless otherwise specified.

With reference to a method disclosed by an example 1 in Chinese patent application CN108697722A, a nicotinamide mononucleotide anhydrous crystal (form 1) was prepared.

With reference to a method disclosed by an example 4 in Chinese patent application CN108697722A, a nicotinamide mononucleotide dimethyl sulfoxide solvate crystal (form 2) was prepared.

Specifically, a method for preparing a nicotinamide mononucleotide cocrystal provided by the present disclosure includes the following two solutions (wherein an organic solvent is tetrahydrofuran, acetonitrile or acetone):

First Solution

An organic solvent was mixed with water in a volume ratio of 1:(1-5) to obtain a mixed system of the organic solvent and the water. The temperature of the mixed system was adjusted to 30-55° C. Nicotinamide mononucleotide and isonicotine were added into the mixed system according to a molar ratio of the nicotinamide mononucleotide to the isonicotine of 1:1 to be uniformly mixed. Then the temperature of the mixed system was lowered to 4-8° C., and standing was performed to wait for crystals to be precipitated.

Second Solution

Nicotinamide mononucleotide and isonicotine were dissolved in water according to a molar ratio of the nicotinamide mononucleotide to the isonicotine of 1:1, and then an organic solvent that accounts for the volume of the water by 0.2-1 time was slowly dropwise added into the water in which the nicotinamide mononucleotide and the isonicotine were dissolved to obtain a mixed system of the organic solvent and the water. During the dropwise adding, the temperature of the mixed system of the organic solvent and the water was kept at 30-55° C., and stirring was performed while dropwise adding. After dropwise adding, the temperature of the mixed system was lowered to 4-8° C., and standing was performed to wait for crystals to be precipitated.

Example 1

A nicotinamide mononucleotide-isonicotine cocrystal was prepared with a method for preparing a nicotinamide mononucleotide cocrystal provided by the present disclosure.

67 g of β-nicotinamide mononucleotide and 24 g of isonicotine were dissolved in 2 L of water, then 2 L of tetrahydrofuran was slowly dropwise added, and stirring was performed while dropwise adding. During the dropwise adding, the temperature of a solution was kept at 45° C. After dropwise adding, the temperature of the solution was lowered to 6° C., and standing was performed to wait for crystals to be precipitated. After crystal precipitation, the solution was filtered to obtain the nicotinamide mononucleotide-isonicotine cocrystal.

Example 2

A nicotinamide mononucleotide-isonicotine cocrystal was prepared with a method for preparing a nicotinamide mononucleotide cocrystal provided by the present disclosure.

67 g of β-nicotinamide mononucleotide and 24 g of isonicotine were dissolved in 2 L of water, then 2 L of acetonitrile was slowly dropwise added, and stirring was performed while dropwise adding. During the dropwise adding, the temperature of a solution was kept at 55° C. After dropwise adding, the temperature of the solution was lowered to 4° C., and standing was performed to wait for crystals to be precipitated. After crystal precipitation, the solution was filtered to obtain the nicotinamide mononucleotide-isonicotine cocrystal.

Example 3

A nicotinamide mononucleotide-isonicotine cocrystal was prepared with a method for preparing a nicotinamide mononucleotide cocrystal provided by the present disclosure.

67 g of β-nicotinamide mononucleotide and 24 g of isonicotine were dissolved in 2 L of water, then 2 L of acetone was slowly dropwise added, and stirring was performed while dropwise adding. During the dropwise adding, the temperature of a solution was kept at 30° C. After dropwise adding, the temperature of the solution was lowered to 8° C., and standing was performed to wait for crystals to be precipitated. After crystal precipitation, the solution was filtered to obtain the nicotinamide mononucleotide-isonicotine cocrystal.

Example 4

A nicotinamide mononucleotide-isonicotine cocrystal was prepared with a method for preparing a nicotinamide mononucleotide cocrystal provided by the present disclosure.

2 L of acetone and 2 L of water were mixed to obtain a mixed solution of the acetone and the water, the temperature of the mixed solution was adjusted to 30° C., 67 g of β-nicotinamide mononucleotide and 24 g of isonicotine were added into the mixed solution, and stirring was performed to dissolve and uniformly mix them. Then the temperature of the mixed solution was lowered to 8° C., and standing was performed to wait for crystals to be precipitated. After crystal precipitation, the solution was filtered to obtain the nicotinamide mononucleotide-isonicotine cocrystal.

Example 5

The nicotinamide mononucleotide-isonicotine cocrystal prepared in the examples 1-4 was subjected to X-ray powder diffraction:

A PANalytical X'Pert Empyrean X-ray powder diffractometer (PW3040/60, Dutch PANalytical Analytical Instruments Ltd.) was used, wherein Cu-Kα radiation is adopted, a wavelength is 1.54 Å, a divergence slit is 1°, a X-ray tube voltage is 45 kV, a X-ray tube current is 40 mA, a scanning range is 2-40° (2θ), a step length is 0.0130°, and step time is 78.7950 s. A powder sample was flattened on a micro-sample plate and then tested. An X-ray powder diffraction spectrum of the nicotinamide mononucleotide-isonicotine cocrystal provided by the present disclosure is as shown in FIG. 1. Peaks and intensities corresponding to a diffraction angle 2θ are as shown in a table 1.

TABLE 1

| 2θ (°) | Relative intensity (%) |
|---|---|
| 9.6 | 15.3 |
| 9.8 | 6.8 |
| 10.6 | 8.9 |
| 13.3 | 100.0 |
| 16.3 | 16.5 |
| 17.1 | 3.1 |
| 19.4 | 4.7 |
| 20.1 | 4.3 |
| 21.3 | 11.9 |
| 21.8 | 5.5 |
| 22.8 | 28.2 |
| 25.7 | 2.5 |
| 26.2 | 3.2 |
| 26.8 | 4.9 |
| 31.4 | 3.7 |
| 32.1 | 15.3 |
| 32.6 | 4.6 |
| 32.9 | 3.5 |
| 36.2 | 6.0 |
| 36.5 | 23.4 |

Example 6

Figure 2:
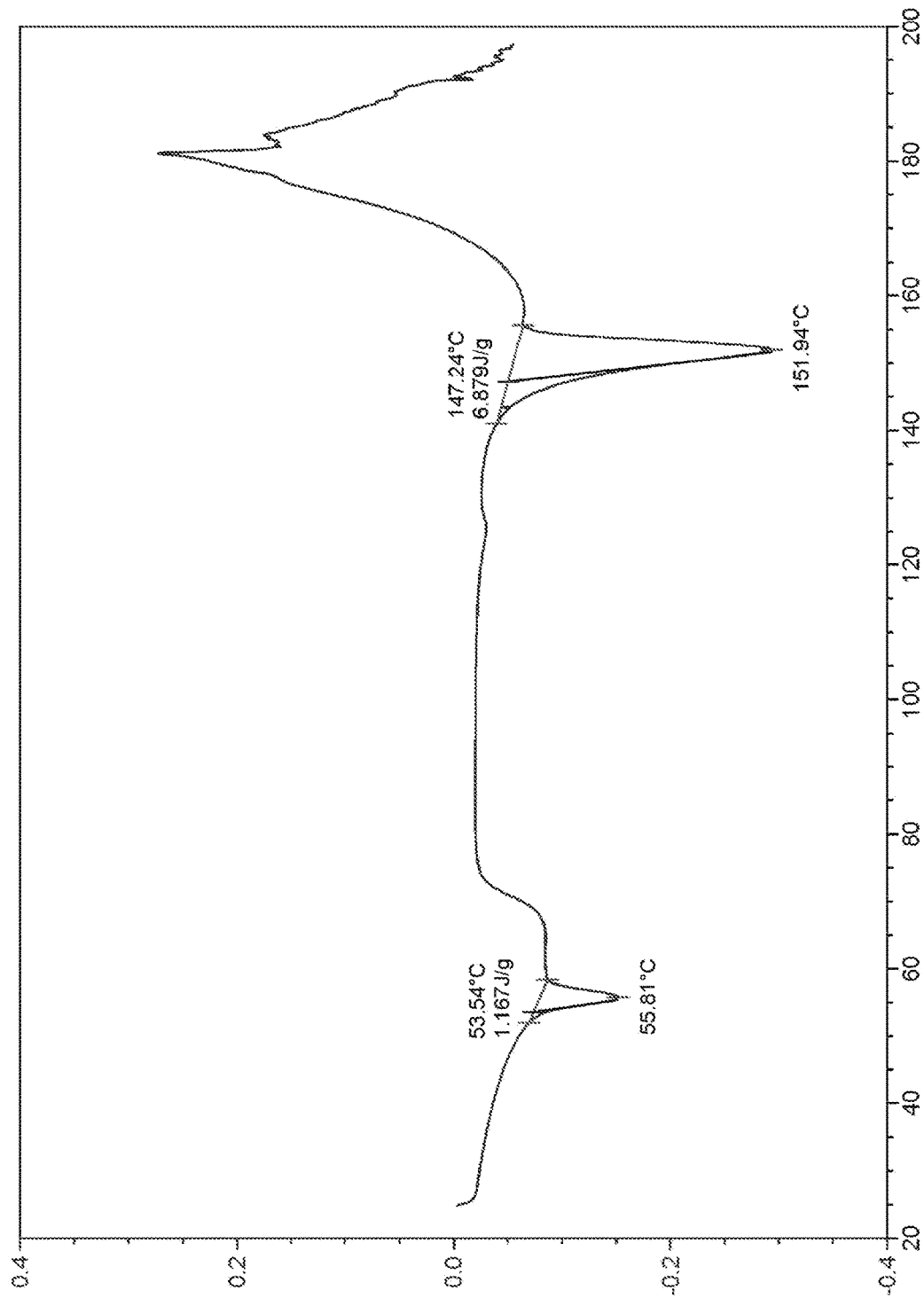
FIG. 2 is a differential scanning calorimetry analysis diagram of the nicotinamide mononucleotide-isonicotine cocrystal provided by the present disclosure.

The nicotinamide mononucleotide-isonicotine cocrystal prepared in the examples 1-4 was subjected to differential scanning calorimetric (DSC) curve measurement:

DSC measurement was performed with a seal plate device in a TA Instruments Q2000. A sample (about 1-3 mg) was weighed in an aluminum plate, capped with a Tzero, accurately recorded to 1/100 mg, and transferred to an instrument for measurement. The instrument was purged with nitrogen at 50 mL/min. Data was collected between room temperature and 220° C. at a heating rate of 10° C./min. Endothermic peaks were plotted downwards, and the data was analyzed with TA Universal Analysis. A differential scanning calorimetry analysis diagram of the nicotinamide mononucleotide-isonicotine cocrystal provided by the present disclosure is as shown in FIG. 2, wherein an abscissa represents the temperature (Temperature, ° C.), and an ordinate represents the heat flow (Heat Flow, W/g) released by a substance per unit mass.

Example 7

Bulk Density Measurement

A proper amount of samples of a crystal in a form 1, a crystal in a form 2 and the nicotinamide mononucleotide-isonicotine cocrystal prepared in the examples 1-4 were taken respectively, screened with a sieve (1.00 mm, No. 18), accurately weighed, and slowly poured into a glass graduated measuring cylinder. The tops were scraped flat. The apparent volumes were recorded. The bulk densities were calculated. Experimental results are as shown in a table 2.

TABLE 2

| Crystal | Bulk density g/ml |
| --- | --- |
| Form 1 | 0.15 |
| Form 2 | 0.22 |
| Cocrystal in example 1 | 0.67 |
| Cocrystal in example 2 | 0.68 |
| Cocrystal in example 3 | 0.68 |
| Cocrystal in example 4 | 0.56 |

Example 8

Content Difference Measurement

A proper amount of a crystal in a form 1, a crystal in a form 2 and the nicotinamide mononucleotide-isonicotine cocrystal prepared in the examples 1-4 were taken respectively and screened with a 200-mesh sieve. A capsule shell was fixed to a capsule board. A body board was filled with powder. The powder was poured on the body board and scraped back and forth with a powder scraping plate. After the capsule shell was filled up with the powder, the excess powder on the body board was scraped off to obtain a capsule. Then the capsule obtained by filling was measured with reference to an inspection method for [content difference] of capsules in the 0103 capsule general principle of the "Pharmacopoeia of the People's Republic of China" (2020 edition). A content difference value X (%) of the content of each capsule corresponding to each group of the crystal in the form 1, the crystal in the form 2 and the cocrystal in the examples 1-4 and average content of the group after comparison was calculated respectively. Then an absolute value of each content difference value was taken. An average value of each group was calculated.

$$\overline{X} = \frac{X1 + X2 + \ldots Xn}{n}.$$

Results are as shown in a table 3.

TABLE 3

| Crystal | Average content difference $\overline{X}$ (%) |
| --- | --- |
| Form 1 | 28.8 |
| Form 2 | 26.0 |
| Cocrystal in example 1 | 5.7 |
| Cocrystal in example 2 | 5.7 |
| Cocrystal in example 3 | 5.5 |
| Cocrystal in example 4 | 8.6 |

The invention claimed is:

1. A method for preparing a nicotinamide mononucleotide cocrystal, comprising the following steps: mixing nicotinamide mononucleotide as an active pharmaceutical ingredient with isonicotine as a cocrystal former by adopting solution synthesis and then performing crystal precipitation, wherein the processes of mixing and crystal precipitation are both performed in a mixed system of an organic solvent and water, and the organic solvent is tetrahydrofuran, acetonitrile or acetone.

2. The method for preparing a nicotinamide mononucleotide cocrystal according to claim 1, wherein the nicotinamide mononucleotide and the isonicotine are mixed in a molar ratio of 1:1.

3. The method for preparing a nicotinamide mononucleotide cocrystal according to claim 1, wherein in the mixed system of the organic solvent and the water, a volume ratio of the organic solvent to the water is 1:(1-5).

4. The method for preparing a nicotinamide mononucleotide cocrystal according to claim 1, wherein during the mixing, the temperature of the mixed system of the organic solvent and the water is kept at 30-55° C.

5. The method for preparing a nicotinamide mononucleotide cocrystal according to claim 1, wherein the mixed system of the organic solvent and the water is obtained by dropwise adding the organic solvent into the water, and before the organic solvent is dropwise added, the nicotinamide mononucleotide and the isonicotine are dissolved in the water.

6. The method for preparing a nicotinamide mononucleotide cocrystal according to claim 5, wherein during the process of dropwise adding the organic solvent into the water, the temperature of the mixed system of the organic solvent and the water is kept at 30-55° C.

7. The method for preparing a nicotinamide mononucleotide cocrystal according to claim 1, wherein the crystal precipitation process is performed in a state where standing is performed after the temperature of the mixed system of the organic solvent and the water is lowered to 4-8° C.

* * * * *